(12) United States Patent
Halstead et al.

(10) Patent No.: US 6,984,331 B2
(45) Date of Patent: Jan. 10, 2006

(54) FILTER CLEANING AND DECONTAMINATING SYSTEM

(75) Inventors: Eric Halstead, Beauport (CA); Serge Coulombe, Boischatel (CA); Eugene Cantin, Chrysostome (CA)

(73) Assignee: Steris Inc., Temecula, CA (US)

( * ) Notice: Subject to any disclaimer, the term of this patent is extended or adjusted under 35 U.S.C. 154(b) by 198 days.

(21) Appl. No.: 10/437,617

(22) Filed: May 14, 2003

(65) Prior Publication Data

US 2004/0226898 A1 Nov. 18, 2004

(51) Int. Cl.
*B01D 29/66* (2006.01)
(52) U.S. Cl. .................. 210/764; 210/791; 422/29
(58) Field of Classification Search ................ 210/248, 210/321.64, 333.01, 411, 636, 791, 797, 798, 210/321.69, 764; 422/28, 29, 31
See application file for complete search history.

(56) References Cited

U.S. PATENT DOCUMENTS

| 3,637,079 | A | * | 1/1972 | Strub ........................ 210/794 |
| 4,872,974 | A | * | 10/1989 | Hirayama et al. ............ 210/90 |
| 4,921,610 | A | * | 5/1990 | Ford et al. .................. 210/636 |
| 5,494,637 | A | * | 2/1996 | Barlow ........................ 422/28 |
| 5,759,289 | A | | 6/1998 | Caron et al. .................. 134/34 |
| 6,408,682 | B2 | | 6/2002 | Greszler ........................ 73/40 |
| 6,412,334 | B1 | | 7/2002 | Kral et al. ..................... 73/40 |
| 6,485,649 | B1 | | 11/2002 | Terävä et al. ............... 210/636 |
| 6,585,943 | B1 | | 7/2003 | Sanford et al. ............. 422/307 |
| 2003/0190256 | A1 | | 10/2003 | Halstead et al. .............. 422/28 |

FOREIGN PATENT DOCUMENTS

WO    WO 01/03813    1/2001

OTHER PUBLICATIONS

U.S. Appl. No. 2002/0163636, published Nov. 7, 2002, to Oberleitner et al., entitled: Endoscope Reprocessing and Sterilization System.

* cited by examiner

*Primary Examiner*—Matthew O. Savage
(74) *Attorney, Agent, or Firm*—Kusner & Jaffe; Michael A. Centanni

(57) ABSTRACT

A system capable of cleaning and disinfecting a filter. A filter element is flushed with a disinfectant solution in a direction opposite to fluid filtration. A filter integrity test checks the integrity of the filter by pressurizing the filter.

9 Claims, 5 Drawing Sheets

US 6,984,331 B2

FILTER CLEANING AND DECONTAMINATING SYSTEM

FIELD OF THE INVENTION

The present invention relates to filtration system for filtering fluids, and more particularly to a filtration system capable of cleaning and decontaminating a filter element.

BACKGROUND OF THE INVENTION

There are many applications in which a filtered fluid is required. For instance, filtered water is used in a fluid microbial decontamination apparatus, for the disinfection or sterilization of medical, pharmaceutical, dental, or mortuary devices, and the like. It is important in this application to minimize the introduction of any impurities into the decontamination apparatus. Accordingly, water is passed through an incoming filter before the water is used in connection with any disinfection or sterilization processes. As the filter is repeatedly used to filter the water, the filter becomes filled with contaminants, thus reducing the effectiveness of the filter. Therefore, it becomes necessary to periodically clean the filter.

The present invention provides an improved filtration system capable of cleaning and decontaminating a filter element.

SUMMARY OF THE INVENTION

In accordance with the present invention there is provided a method for operating a filter including: (a) a first chamber having a first inlet port in communication with a source of a fluid to be filtered; (b) a second chamber having at least one filter port; (c) a filter element disposed between the first chamber and the second chamber; and (d) a first outlet port in communication with a drain, the method comprising the steps of: (1) receiving the fluid into the filter through the first inlet port; (2) passing the fluid in the filter through the filter element, from the first chamber to the second chamber, to provide a filtered fluid; (3) removing the filtered fluid from the second chamber through said at least one filter port; (4) closing the first inlet port; (5) opening the first outlet port to drain the filter; (6) receiving disinfectant solution into the filter through the at least one filter port; and (7) passing the disinfectant solution through the filter element, from the second chamber to the first chamber, to effect cleaning of the filter element.

In accordance with another aspect of the present invention, there is provided a method for operating a filter including: (a) a first chamber; (b) a second chamber; and (c) a filter element disposed between the first chamber and the second chamber, said method comprising the steps of: (1) passing a fluid through the filter element, from the first chamber to the second chamber; (2) draining fluid from the filter; and (3) backflushing the filter element by passing a disinfectant solution through the filter element, from the second chamber to the first chamber.

In accordance with still another aspect of the present invention, there is provided a filtration system, comprising: (a) a first chamber having a first inlet port in communication with a source of a fluid to be filtered; (b) a second chamber having at least one filter port for receiving a disinfectant solution; (c) a filter element disposed between the first chamber and the second chamber; and (d) a first outlet port in communication with a drain; wherein the fluid is filtered by passing the fluid through the filter element, from the first chamber to the second chamber, and the filter element is cleaned by passing the disinfectant solution through the filter element, from the second chamber to the first chamber.

In accordance with yet another aspect of the present invention, there is provided a method for operating a filter including: (a) a first chamber; (b) a second chamber; and (c) a filter element disposed between the first chamber and the second chamber, said method comprising the steps of: (1) forcing compressed air into the first chamber; (2) pressurizing the first chamber to a predetermined pressure; (3) sensing a pressure decay in the first chamber, as the compressed air passes through the filter element into the second chamber; (4) and determining the integrity of the filter in accordance with the sensed pressure decay.

An advantage of the present invention is the provision of a filtration system that effectively cleans and decontaminates the filter by exposing the filter to a decontamination fluid.

Another advantage of the present invention is the provision of a method for cleaning and decontaminating a filter by exposing the filter to a decontamination fluid.

Still another advantage of the present invention is the provision of a filtration system that monitors the integrity of the filter.

These and other advantages will become apparent from the following description of a preferred embodiment taken together with the accompanying drawings and the appended claims.

BRIEF DESCRIPTION OF THE DRAWINGS

The invention may take physical form in certain parts and arrangement of parts, a preferred embodiment of which will be described in detail in the specification and illustrated in the accompanying drawings which form a part hereof, and wherein.

DETAILED DESCRIPTION OF A PREFERRED EMBODIMENT

It should be appreciated that while the present invention is described herein with particular reference to a filtration system 10 used in connection with an exemplary fluid microbial decontamination system 5, it is not intended to limit the same. In this regard, it is contemplated that the present invention finds utility with a wide variety of systems requiring the filtration of fluids.

Figure 3:
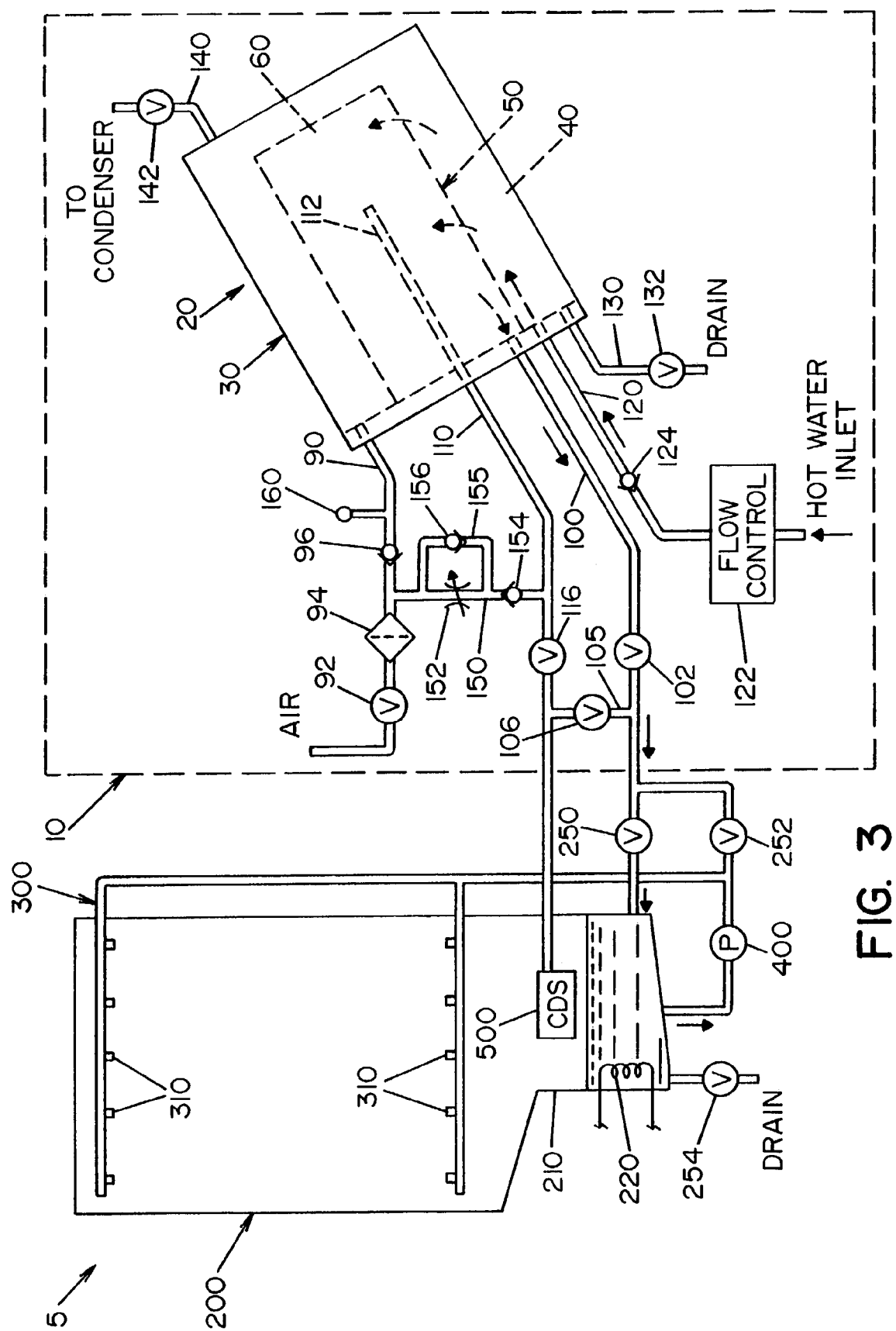
FIG. 3 is a schematic view of the filtration system shown in FIG. 1 as used in connection with an exemplary fluid microbial system, during a fill mode operation.
Figure 4:
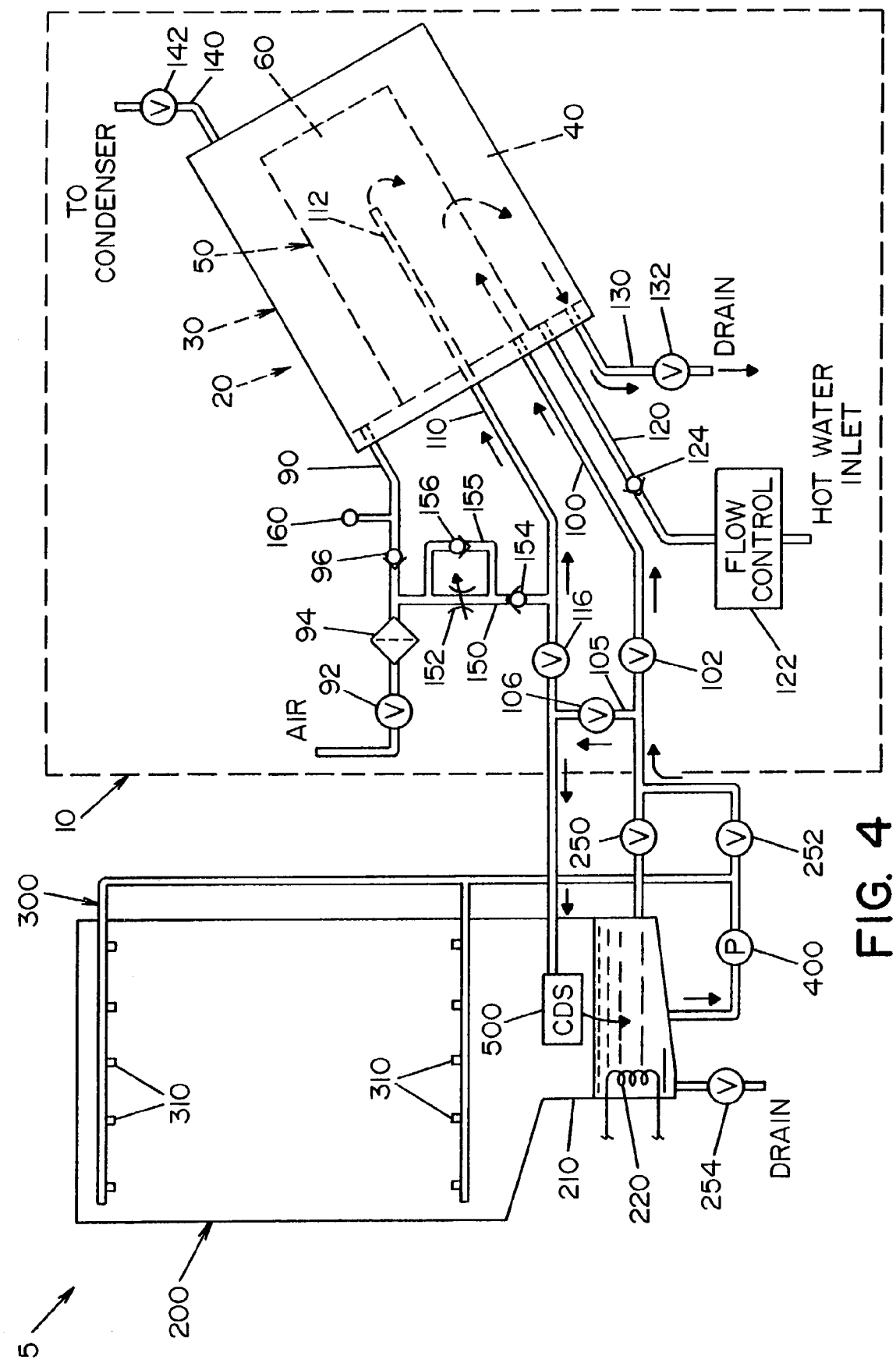
FIG. 4 is a schematic view of the filtration system shown in FIG. 1 as used in connection with an exemplary fluid microbial system, during a circulation mode operation.
Figure 5:
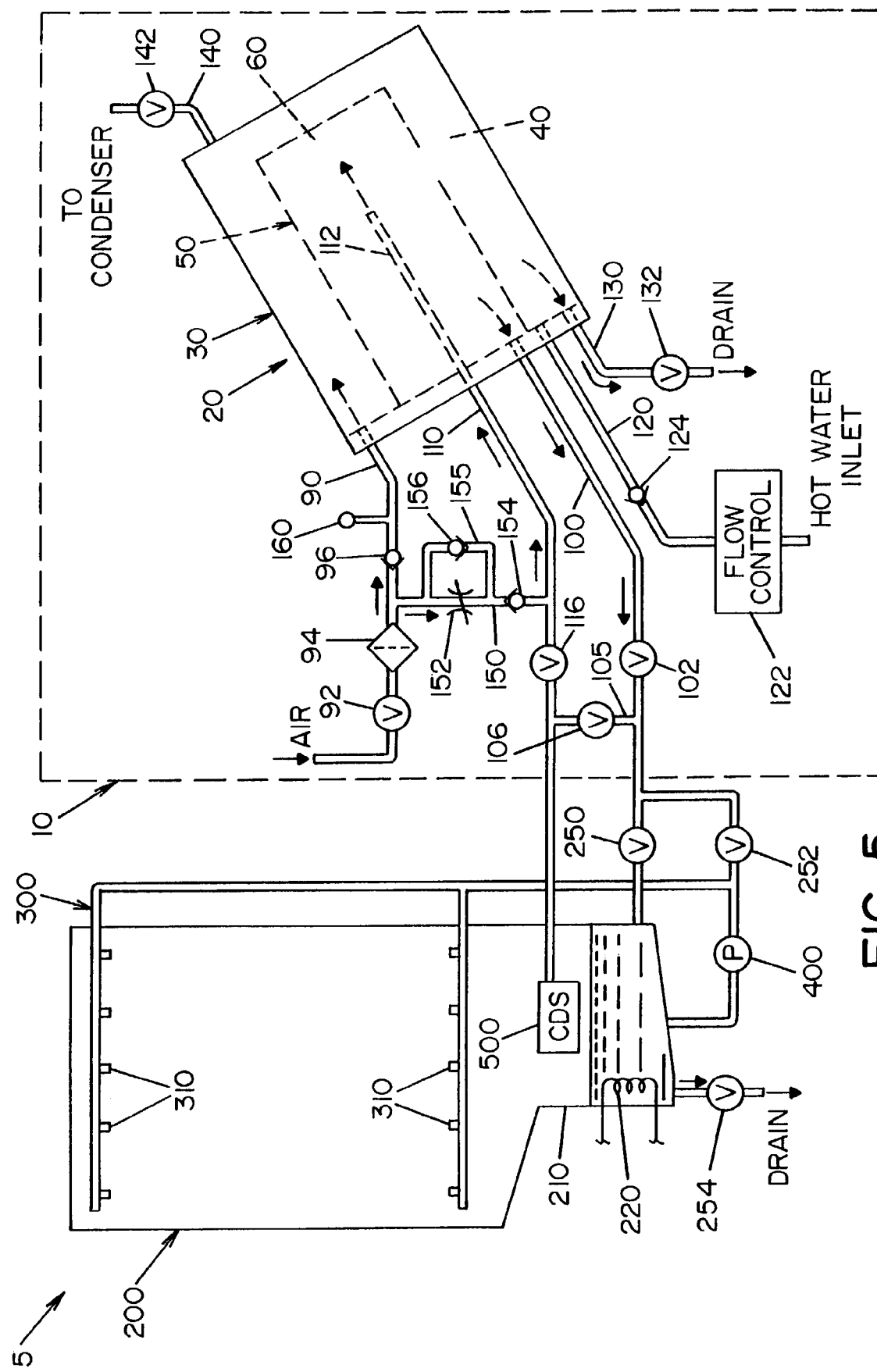
FIG. 5 is a schematic view of the filtration system shown in FIG. 1 as used in connection with an exemplary fluid microbial system, during a drain mode operation.

Referring now to the drawings wherein the showings are for the purposes of illustrating a preferred embodiment of the invention only and not for purposes of limiting same, FIGS. 3–5 show a filtration system 10, according to a preferred embodiment of the present invention, in connection with an exemplary fluid microbial decontamination system 5. Fluid microbial decontamination system 5 is generally comprised of a washing chamber 200, a spray system 300, a circulation pump 400, and a chemical disinfectant system (CDS) 500. Washing chamber 200 includes a sump 210 where fluid collects. A heating element 220 is provided to heat the fluid collected in sump 210. Sprayer system 300 includes a plurality of nozzles 310 that dispense fluid into washing chamber 200. Circulation pump 400 pumps fluid from sump 210 throughout the system, as will be described in further detail below. Valves 250, 252 and 254 control the flow of fluid along a plurality of fluid paths of fluid microbial decontamination system 5. It should be appreciated that fluid microbial decontamination system 5 may include many additional fluid paths not described herein.

CDS 500 includes a housing (not shown) for holding a cartridge or cup (not shown) containing a disinfectant concentrate or reagents that reacts with a fluid (e.g., filtered water) to form a disinfectant solution. The disinfectant solution is supplied to washing chamber 200, wherein objects (e.g., medical instruments) are exposed to the disinfectant solution to effect microbial decontamination of the objects. The disinfectant solution is also supplied to filtration system 10 in accordance with the present invention, as will be described in detail below.

Figure 1:
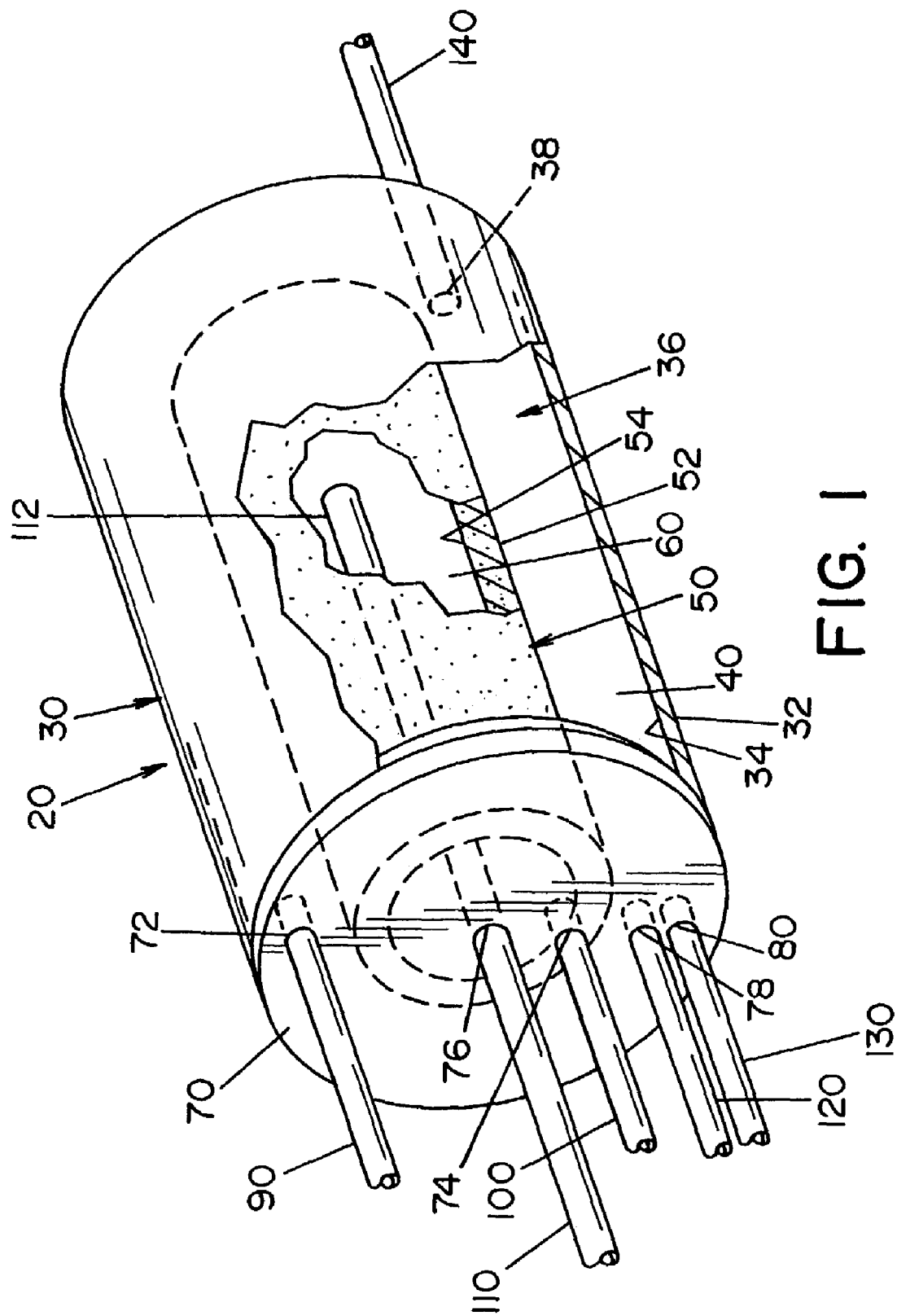
FIG. 1 is a perspective view of a filtration system, including a filter, partially broken to show the interior thereof.
Figure 2:
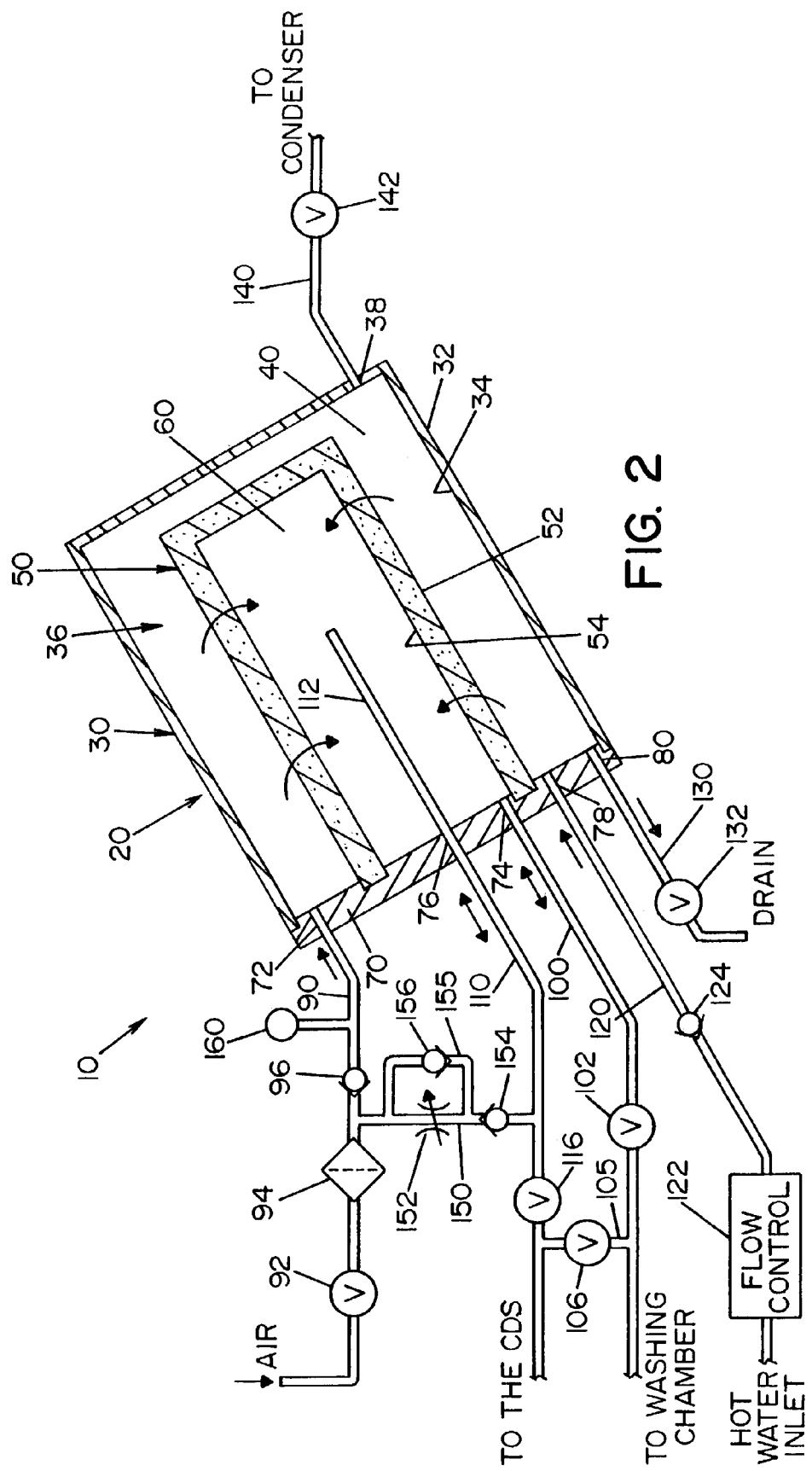
FIG. 2 is a schematic view of the filtration system shown in FIG. 1.

Referring now to FIGS. 1 and 2, there is shown a filter 20, according to a preferred embodiment of the present invention. FIG. 2 is a detailed schematic view of filtration system 10 including filter 20.

Filter 20 generally comprised of an outer housing 30, a filter element 50, and a base 70. Outer housing 30 has an outer surface 32 and an inner surface 34. Outer housing 30 is fixed to base 70, to form a fluid-tight container that defines a cavity 36.

Filter element 50 has an outer surface 52 and an inner surface 54. Filter element 50 is located within cavity 36 defined by outer housing 30. Filter element 50 is also attached to base 70. In a preferred embodiment, filter element 50 is a generally cylindrical structure made of a relatively dense filtration media. In a preferred embodiment, the filtration media is dimensioned to filter particles in the range of 0.1 to 0.5 microns, and more preferably about 0.2 microns. One exemplary filtration media is the Pall MCY4463DFLPH4 filter cartridge from Pall Corporation. This filter cartridge is a Fluorodyne II hydrophilic PVDF (double layer) filtration media, with a microbial removal rating of 0.2 $\mu$m, sterilizing grade.

With reference to FIG. 2, an outer chamber 40 is defined between housing 30 and filter element 50. An inner chamber 60 is defined by inner surface 54 of filter element 50.

Base 70 includes a plurality of ports 72, 74, 76, 78, 80 for fluid communication with filter 20. In this regard, first port 72 is connected to an air line 90 providing fluid communication between outer chamber 40 and a compressed air source. A control valve 92, air filter 94 and (directional) check valve 96 are disposed in line 90, to control the flow and direction of air flow in line 90, as will be described in further detail below. Check valve 96 only allows fluid flow into filter 20. In a preferred embodiment, air filter 94 is a 0.2 micron filter.

Second port 74 connects with a fluid line 100, providing fluid communication with the fluid microbial decontamination system 5, as schematically illustrated in the drawings. A control valve 102 is located along fluid line 100. In a preferred embodiment, control valve 102 is constructed to allow "counter flow" when it is closed (i.e., not energized). In this respect, valve 102 allows fluid flow out of filter 20 through fluid line 100 when it is closed, but only allows fluid flow into filter 20 through fluid line 100 when it is open (i.e., energized).

Port 76 connects with a fluid line 110, providing fluid communication between inner chamber 60 and a chemical disinfectant system (CDS) 500. A control valve 116 is located along CDS line 110. In a preferred embodiment, a portion 112 of fluid line 110 extends into inner chamber 60.

Port 78 connects with a water line 120, providing fluid communication between outer chamber 40 and a water inlet. In a preferred embodiment, water inlet supplies heated water. Water travels along line 120 from the water inlet to outer chamber 40. In a preferred embodiment, a flow control 122 and a (directional) check valve 124 are located along line 120. Flow control 122 controls the flow of water from the water inlet into outer chamber 40. Check valve 124 only allows fluid flow into filter 20.

Port 80 connects with a drain line 130 providing fluid communication between outer chamber 40 and a drain. Fluid travels along drain line 130 from outer chamber 40 to the drain. A control valve 132 is located along drain line 130 to control the flow of fluid to the drain.

An optional port 38 is also formed in outer housing 30. Port 38 communicates with a condenser line 140, providing fluid communication between outer chamber 40 and a condenser system. The condenser system preferably includes a direct contact cold-water condenser. A control valve 142 is provided along condenser line 140 to control the flow of fluid to the condenser.

A line 150 is disposed between line 90 and line 110, to provide fluid communication therebetween. In a preferred embodiment, line 150 connects with line 90 between air filter 94 and check valve 96, and connects with line 110 between control valve 116 and port 76. A needle valve 152 and check valve 154 are located along connecting line 150. A return (bypass) line 155 is provided in connection with needle valve 152. Return line 155 includes a check valve 156. The return line 155 regulates a high pressure condition associated with needle valve 152. In this regard, if the pressure associated with fluid flowing through needle valve 152 exceeds a predetermined amount, fluid will flow along return line 155 to prevent a high pressure condition.

A line 105 is disposed between lines 100 and 110, to provide fluid communication therebetween. In a preferred embodiment, line 105 connects with line 100 between control valve 102 and washing chamber 200, and connects with line 110 between control valve 116 and CDS 500. A control valve 106 is located in line 105.

In a preferred embodiment, control valves 92, 102, 106, 116, 132 and 142 are solenoid-actuated.

A control unit (not shown) controls the operation of control valves 92, 102, 106, 116, 132, 142, and 152, the air source, and flow control 122 associated with the water inlet. In a preferred embodiment, the control unit takes the form of a microcontroller or microcomputer. This same control unit preferably controls circulation pump 400, valves 250, 252 and 254, as well as other components of fluid microbial decontamination system 5.

In a preferred embodiment of the present invention, filter 20 is angled to direct fluid flow (of liquids) toward port 80 associated with drain line 130. This facilitates the exit of liquids from outer and inner chambers 40, 60.

Operation of filtration system 10 will now be described in detail with particular reference to FIGS. 3–5. It should be understood that the operating method of filtration system 10 as disclosed herein illustrates a preferred embodiment of the present invention, and is not intended to limit the same.

Fluid microbial decontamination system 5 may perform one or more of the following operations: (1) a fill mode wherein sump 210 is filled with filtered water, (2) a dissolution mode wherein disinfectant concentrate is dissolved with filtered water in CDS 500 to form a disinfectant solution (e.g., peracidic acid), (3) a backflow filter cleaning mode wherein disinfectant is circulated in filter 20 to clean and disinfect filter element 50, (4) a rinse mode wherein rinse water is circulated through washing chamber 200, (5) a drain mode wherein filter 20 and washing chamber 200 are drained, and (6) a filter test mode wherein the integrity of filter 20 is tested.

The fill mode will now be described with reference to FIG. 3. Starting with filter 20 empty, and valves 92, 102, 106, 116, 132, 142 and 152 closed, flow control 122 is controlled to allow heated water from the water inlet to enter outer chamber 40 through water line 120. In this respect, the water pressure along water line 120 forces directional check valve 124 open, thus allowing the heated water to flow into outer chamber 40. The heated water filling outer chamber 40 passes through filter element 50 (from outer surface 52 to inner surface 54) and into inner chamber 60 as filtered water. Accordingly, the heated water is filtered by filter element 50 as it passes therethrough. The filtered water filling inner chamber 60 exits inner chamber 60 through line 100. As indicated above, valve 102 is constructed to allow "counter flow" when it is closed. Therefore, as filtered water enters inner chamber 60 of filter 20, water pressure is applied to the exit side of valve 102. Consequently, filtered water exits inner chamber 60 by counter flowing through valve 102. In a preferred embodiment, valves 250 and 252 are controlled to allow the filtered water to flow to sump 210, and to be subsequently pumped by circulation pump 400. Once sump 210 has been filled to a desired level, flow control 122 is closed to prevent the further flow of heated water into filter 20.

It should be understood that upon initial flow of heated water into filter 20, control valve 142 may be momentarily opened (e.g., 1–5 seconds) to allow any air inside filter 20 pass out through condenser line 140 to the condenser. Thereafter, valve 142 is closed.

In the dissolution mode, disinfectant concentrate is dissolved with filtered water to form a disinfectant solution by supplying filtered water to CDS 500. To this end, valve 106 is opened, while keeping valves 102 and 116 closed. Accordingly, filtered water pumped by circulation pump 400 can travel from circulation pump 400 to CDS 500 without entering filter 20. At CDS 500, the filtered water mixes with the disinfectant concentrate to form the disinfectant solution. In a preferred embodiment, flow control 122 is controlled to stop water from entering filter 20 while valve 106 is opened.

The backflow filter cleaning mode will now be described with reference to FIG. 4. Disinfectant solution from CDS 500 may be introduced into filter 20 in a backflow operation, to clean and disinfect filter element 50. To this end, flow control 122 is controlled to close the flow of water from the water inlet. Furthermore, drain valve 132 is opened to allow water remaining in filter 20 to flow out through drain line 130 into the drain. As a result, water will be removed from outer chamber 40. Valve 106 remains open, and valves 102 and 116 are opened to allow disinfectant solution to flow into inner chamber 60 through lines 110 and 100. The disinfectant solution filling inner chamber 60 passes through filter element 50 (from inner surface 54 to outer surface 52) into outer chamber 40. Disinfectant solution in outer chamber 40 exits filter 20 through drain line 130.

It should be appreciated that filter cleaning is facilitated by the removal of water from outer chamber 40 by controlling the operation of drain valve 132. In this regard, removal of water eliminates the "concentration gradient" through filter element 50, normally occurring when water is present in outer chamber 40, as disinfectant solution passes through filter element 50. The filter cleaning allows disinfectant solution to permeate completely through filter element 50. The "concentration gradient" results from the mixing of the disinfectant solution with the residual water in outer chamber 40. Consequently, a concentration gradient occurs as the disinfectant solution becomes more diluted, as it passes from inner chamber 60 to outer chamber 40.

During the rinse mode, circulating pump 400 circulates rinse water through washing chamber 200. To isolate filter 20 from the rinse water, valves 102, 106 and 116 are closed. Since the bacterial content of the rinse water is unknown, it is undesirable to introduce the rinse water into filter 20. However, new supplies of filtered water can be provided to circulation pump 200 during circulation of rinse water through washing chamber 200. In this regard, flow control 122 is controlled to allow heated water to flow into filter 20. This heated water is filtered (as described above), and flows out of filter 20 through line 100 to fluid microbial decontamination system 5. As indicated above, filtered water exiting filter 20 can pass through valve 102 when closed.

The drain mode will now be described with reference to FIG. 5. When washing chamber 200 is to be drained, it is also desirable to drain filter 20. In this regard, flow control 122 is controlled to prevent the flow of heated water to filter 20 via line 120. Drain valve 132 is then opened to drain water from filter 20. Water remaining in filter 20 is removed by opening control valve 92 and activating the air source to supply air to filter 20 through air line 90. In this regard, the air pressure along air line 90 forces check valve 96 open, allowing air to pass into outer chamber 40, thus pressurizing outer chamber 40. The forced air evacuates water remaining in outer chamber 40 by forcing the water into drain line 130 and into the drain. Needle valve 152 is also opened to allow air from the air source to enter inner chamber 60, thus pressurizing inner chamber 60. In this regard, air pressure along line 150 forces check valve 154 open, allowing air to pass into inner chamber 60 via line 110. Residual water in inner chamber 60 exits filter 20 "counter flow" through line 100. It should be understood that valves 102, 106, and 116 remain closed during this draining operation.

In the filter test mode the integrity of filter 20 is checked. In this operating mode, drain valve 132 is closed, condenser valve 142 is closed, flow control 122 is controlled to prevent any incoming water, and valves 152, 106 and 116 are closed. Valve 92 is then opened to allow air from the air source to enter outer chamber 40 through air line 90. A pressure sensor 160 (e.g., a pressure transducer), located along line 90 is used to monitor the pressure within outer chamber 40. In a preferred embodiment, outer chamber 40 is pressurized to a predetermined pressure (e.g., about 40 psi). Pressure sensor 160 is used to monitor a pressure decay resulting from gas diffusion through filter element 50, and determine the operational status of filter 20. Pressure sensor 160 is preferably connected with the control unit described above. The control unit may include a visual or audible indicators for indicating to the operator the success or failure of the filter integrity test. After the filter integrity test is completed, pressure in filter 20 is released by opening valve 142, and releasing the air to the condenser.

The present invention provides improved cleaning of filter 20 because the direction of fluid flow through filter element 50 for the disinfectant solution is opposite to the direction of fluid flow through filter element 50 for filtration of the heated water during a filtration operation. Moreover, water is removed from filter 20 before disinfectant solution is moved through filter element 50, thus eliminating a concentration gradient of the disinfectant solution.

Other modifications and alterations will occur to others upon their reading and understanding of the specification. It is intended that all such modifications and alterations be included insofar as they come within the scope of the invention as claimed or the equivalents thereof.

Having described the invention, the following is claimed:

1. A method for operating a filter in a fluid microbial decontamination system, the filter including: (a) a first chamber having a first inlet port in communication with a source of a fluid to be filtered and a first outlet port in communication with a drain; (b) a second chamber having at least one filter port; and (c) a filter element disposed between the first chamber and the second chamber, the method comprising:
   receiving the fluid into the filter through the first inlet port;
   passing the fluid in the filter through the filter element, from the first chamber to the second chamber, to provide a filtered fluid;
   removing the filtered fluid from the second chamber through said at least one filter port;
   closing the first inlet port;
   opening the first outlet port to drain fluid from the filter;
   receiving disinfectant solution into the filter through the at least one filter port, said disinfectant solution produced by combining filtered fluid removed from the second chamber with a disinfectant concentrate;
   passing the disinfectant solution through the filter element, from the second chamber to the first chamber, to effect cleaning of the filter element; and
   removing the disinfectant solution from the filter through the first outlet port.

2. A method according to claim 1, wherein the method further comprises the step of receiving compressed gas into the filter.

3. A method according to claim 2, wherein said compressed gas is received into the filter through a second inlet port in communication with said first chamber, forcing fluid out of said first chamber through the first outlet port.

4. A method according to claim 2, wherein said compressed gas is received into said second chamber through a first of said at least one filter ports, forcing fluid out of said second chamber through a second of said at least one filter port.

5. A method according to claim 2, wherein said compressed gas is filtered before receipt into said filter.

6. A method according to claim 1, wherein said fluid is water.

7. A method according to claim 2, wherein said compressed gas is air.

8. A method according to claim 1, wherein said first chamber is an outer chamber, and said second chamber is an inner chamber.

9. A method according to claim 1, wherein said first outlet port is in communication with said first chamber.

* * * * *